(12) United States Patent
Moll et al.

(10) Patent No.: US 8,300,993 B2
(45) Date of Patent: Oct. 30, 2012

(54) WAVEGUIDE WITH INTEGRATED LENS

(75) Inventors: Kevin D. Moll, Boulder, CO (US); Kurt R. Vogel, Boulder, CO (US); Marie J. Delaney, Boulder, CO (US); Michael J. Lochhead, Boulder, CO (US); Christopher J. Myatt, Boulder, CO (US)

(73) Assignee: MBio Diagnostics, Inc., Boulder, CO (US)

( * ) Notice: Subject to any disclaimer, the term of this patent is extended or adjusted under 35 U.S.C. 154(b) by 0 days.

(21) Appl. No.: 12/617,535

(22) Filed: Nov. 12, 2009

(65) Prior Publication Data

US 2010/0220318 A1 Sep. 2, 2010

Related U.S. Application Data

(60) Provisional application No. 61/156,586, filed on Mar. 2, 2009.

(51) Int. Cl.
*G02B 6/12* (2006.01)
(52) U.S. Cl. .......................................... 385/14
(58) Field of Classification Search ........................ None
See application file for complete search history.

(56) References Cited

U.S. PATENT DOCUMENTS

| | | | |
|---|---|---|---|
| 4,608,344 A | 8/1986 | Carter et al. | |
| 4,746,179 A | 5/1988 | Dahne et al. | |
| 4,810,658 A * | 3/1989 | Shanks et al. | 436/172 |
| 4,849,340 A | 7/1989 | Oberhardt | |
| 4,852,967 A | 8/1989 | Cook et al. | |
| 4,978,503 A | 12/1990 | Shanks et al. | |
| 5,120,131 A * | 6/1992 | Lukosz | 356/481 |
| 5,166,515 A * | 11/1992 | Attridge | 250/227.25 |
| 5,227,134 A | 7/1993 | Janata | |
| 5,344,784 A | 9/1994 | Attridge | |
| 5,469,264 A * | 11/1995 | Shigemori | 356/417 |
| 5,496,700 A | 3/1996 | Ligler et al. | |
| 5,599,668 A | 2/1997 | Stimpson et al. | |
| 5,677,196 A * | 10/1997 | Herron et al. | 436/518 |
| 5,747,274 A | 5/1998 | Jackowski | |
| 5,766,957 A * | 6/1998 | Robinson et al. | 436/165 |
| 5,832,165 A | 11/1998 | Reichert et al. | |

(Continued)

FOREIGN PATENT DOCUMENTS

AU 768800 9/2001

(Continued)

OTHER PUBLICATIONS

Axelrod, D., "Cell-Substrate Contacts Illuminated by Total Internal Reflection Fluorescence", "The Journal of Cell Biology", Apr. 1, 1981, pp. 141-145, vol. 89, Number Apr. 1981, Publisher: The Rockefeller University Press.

(Continued)

*Primary Examiner* — Sung Pak
(74) *Attorney, Agent, or Firm* — Lathrop & Gage LLP

(57) ABSTRACT

A sample can be illuminated for analysis using apparatus including a light source, a planar waveguide, and a refractive volume. The light source provides light along a propagation vector. The planar waveguide is oriented such that the propagation vector is perpendicular to the normal vector of the planar waveguide and offset from the planar waveguide in a direction parallel to the normal vector of the planar waveguide. The refractive volume is positioned proximate to the planar waveguide and can optically coupling light provided by the light source to the planar waveguide.

38 Claims, 7 Drawing Sheets

U.S. PATENT DOCUMENTS

| | | | |
|---|---|---|---|
| 5,843,651 A | | 12/1998 | Stimpson et al. |
| 5,846,842 A | * | 12/1998 | Herron et al. .................. 436/518 |
| 5,858,800 A | * | 1/1999 | Shigemori et al. ............ 436/518 |
| 5,919,712 A | * | 7/1999 | Herron et al. .................. 436/518 |
| 5,959,292 A | | 9/1999 | Duveneck et al. |
| D426,783 S | | 6/2000 | Christensen et al. |
| 6,108,463 A | | 8/2000 | Herron et al. |
| 6,137,117 A | | 10/2000 | Feldstein et al. |
| 6,192,168 B1 | * | 2/2001 | Feldstein et al. ................. 385/12 |
| 6,222,619 B1 | | 4/2001 | Heron et al. |
| 6,242,267 B1 | | 6/2001 | Herron et al. |
| 6,287,871 B1 | | 9/2001 | Herron et al. |
| 6,316,274 B1 | | 11/2001 | Herron et al. |
| 6,356,676 B1 | | 3/2002 | Herron et al. |
| 6,384,912 B2 | | 5/2002 | Kraus et al. |
| 6,395,558 B1 | | 5/2002 | Duveneck et al. |
| 6,485,905 B2 | | 11/2002 | Hefti |
| 6,574,390 B2 | | 6/2003 | Kropp |
| 6,596,545 B1 | | 7/2003 | Wagner et al. |
| 6,611,634 B2 | * | 8/2003 | Herron et al. .................... 385/12 |
| 6,682,942 B1 | | 1/2004 | Wagner et al. |
| 6,686,208 B2 | | 2/2004 | Meusel et al. |
| 6,767,733 B1 | | 7/2004 | Green |
| 6,847,746 B2 | | 1/2005 | Uchiyama |
| 6,861,251 B2 | | 3/2005 | Green |
| 6,951,715 B2 | | 10/2005 | Cunningham et al. |
| 6,954,580 B2 | | 10/2005 | Soskind et al. |
| 6,961,490 B2 | | 11/2005 | Maisenhoelder et al. |
| 6,979,567 B2 | | 12/2005 | Herron et al. |
| 6,984,491 B2 | | 1/2006 | Mirkin et al. |
| 7,022,515 B2 | | 4/2006 | Herron et al. |
| 7,056,676 B2 | | 6/2006 | Korlach et al. |
| 7,175,811 B2 | * | 2/2007 | Bach et al. .................. 422/82.11 |
| 7,189,361 B2 | | 3/2007 | Carson et al. |
| 7,202,076 B2 | | 4/2007 | Cunningham et al. |
| 7,236,666 B2 | | 6/2007 | Towle et al. |
| 7,248,361 B2 | | 7/2007 | Kiesel et al. |
| RE39,772 E | | 8/2007 | Herron et al. |
| 7,268,868 B2 | | 9/2007 | Kiesel et al. |
| 7,276,368 B2 | | 10/2007 | Saaski |
| 7,327,454 B2 | | 2/2008 | Cunningham et al. |
| 7,368,281 B2 | | 5/2008 | Mozdy et al. |
| 7,456,953 B2 | | 11/2008 | Schmidt et al. |
| 7,496,245 B2 | | 2/2009 | Saaski |
| 7,522,811 B2 | | 4/2009 | Schmidt et al. |
| 7,529,438 B2 | | 5/2009 | Schmidt et al. |
| 2005/0036728 A1 | | 2/2005 | Braunisch |
| 2006/0068412 A1 | | 3/2006 | Tang |
| 2006/0188873 A1 | | 8/2006 | Abel et al. |
| 2007/0189668 A1 | * | 8/2007 | Payne ............................. 385/33 |
| 2008/0219616 A1 | | 9/2008 | Wimberger-Friedl et al. |
| 2010/0220318 A1 | | 9/2010 | Moll et al. |

FOREIGN PATENT DOCUMENTS

| | | |
|---|---|---|
| CA | 2069539 A1 | 12/1992 |
| CA | 2162996 | 11/1994 |
| CA | 2248189 | 9/1997 |
| CA | 2303794 | 3/1999 |
| EP | 0519623 B1 | 8/1998 |
| EP | 0700514 B1 | 11/2001 |

OTHER PUBLICATIONS

Axelrod, D., "Total Internal Reflection Fluorescence Microscopy in Cell Biology", "Traffic 2001", Nov. 2001, pp. 764-774, vol. 2, No. 11, Publisher: Munksgaard International Publishers.

Desmat, T., et al., "Nonthermal Plasma Technology as a Versatile Strategy for Polymeric Biomaterials Surface Modification: A Review", "BioMacromolecules", Sep. 2009, p. 28 vol. 10, No. 9, Publisher: American Chemical Society, Published in: US.

Duveneck, G.L, et al., "Planar Waveguides for Ultra-High Sensitivity of the Analysis of Nucleic Acids", "Analytica Chimica Acta", 2002, pp. 49-61, vol. 469, Publisher: Elsevier Science B.V.

Golden, J.P., et al., "A Comparison of Imaging Methods for use in an Array Biosensor", "Biosensors and Bioelectronics", 2002, pp. 719-725, vol. 17, Publisher: Elsevier Science B.V.

Grandin, H.M., et al., "Waveguide Excitation Fluorescence Microscopy: A New Tool for Sensing and Imaging the Biointerface", "Biosensors and Bioelectronics", 2006, pp. 1476-1482, vol. 21, Publisher: Elsevier B.V.

Herron, J.N., et al., "Fluorescent Immunosensors Using Planar Waveguides", "Advances in Fluorescence Sensing Technology", 1993, pp. 28-39, vol. 1885, Publisher: SPIE, Published in: US.

Ligler, F.S., et al., "Array Biosensor for Detection of Toxins", "Analytical and Bioanalytical Chemistry", Jun. 13, 2003, pp. 469-477, vol. 377, Publisher: Springer-Verlag.

Ligler, F.S., et al., "Integrating Waveguide Biosensor", "Analytical Chemistry", Feb. 1, 2002, pp. 713-719, vol. 74, No. 3, Publisher: American Chemical Society.

Liron, Z., et al., "Voltage-Induced Inhibition of Antigen-Antibody Binding at Conducting Optical Waveguides", "Biosensors and Bioelectronics", 2002, pp. 489-494, vol. 17, Publisher: Elsevier Science B.V.

Lundgren, J.S., et al., "A Liquid Crystal Pixel Array for Signal Discrimination in Array Biosensors", "Biosensors and Bioelectronics", 2000, pp. 417-421, vol. 15, Publisher: Elsevier Science S.A.

Myers, F.B., et al., "Innovations in Optical Microfluidic Technologies for Point-of-Care Diagnostics", "Lab on a Chip", Oct. 30, 2008, pp. 2015-2031, vol. 8, Publisher: The Royal Society of Chemistry.

O'Brien, T., et al., "The Development of Immunoassays to Four Biological Threat Agents in a Bidiffractive Grating Biosensor", "Biosensors and Bioelectronics", 2000, pp. 815-828, vol. 14, Publisher: Elsevier Science S.A.

Okagbare, P.I., et al., "Fabrication of a Cyclic Olefin Copolymer Planar Waveguide Embedded in a Multi-Channel Poly (methyl methacrylate) Fluidic Chip for Evanescence Excitation", "Lab on a Chip", Nov. 4, 2009, pp. 66-73, vol. 10, Publisher: The Royal Society of Chemistry.

Young, Lee W., "Notification of Transmittal of the International Search Report/Written Opinion of the International Searching Authority re PCT/US10/25172", Nov. 8, 2010, Published in: PCT.

Rowe-Taitt, C., et al., "Evanescent Wave Fluorescence Biosensors", "Biosensors and Bioelectronics", 2005, pp. 2470-2487, vol. 20, Publisher: Elsevier B.V.

Schmidt, H., et al., "Optofluidic Waveguides: I. Concepts and Implementations", "Microfluid Nanofluid", 2008, pp. 3-16, vol. 4, Publisher: Springer-Verlag.

TIRF Technologies, "Shallow Angle Fluorescence Microscopy", Nov. 10, 2010, p. 1 Publisher: TIRF Technologies, Inc.

* cited by examiner

WAVEGUIDE WITH INTEGRATED LENS

CROSS REFERENCE TO RELATED APPLICATION

This application claims the priority benefit of U.S. provisional patent application No. 61/156,586 filed Mar. 2, 2009 and entitled "Waveguide with Integrated Lens," the disclosure of which is incorporated herein by reference.

GOVERNMENT INTEREST

This invention was made with government support under contract 70NANB7H7053 awarded by the U.S. Department of Commerce. The Government has certain rights in this invention.

BACKGROUND OF THE INVENTION

1. Field of the Invention

The present invention generally relates to waveguides for sample illumination. More specifically, the present invention relates to planar waveguides proximate to refractive volumes.

2. Description of the Related Art

Fluorescently labeled probes provide a convenient method of characterizing the content of biological samples. By tailoring binding chemistry of a fluorescent probe, high specificity can be achieved for detection of complex molecules such as RNA, DNA, proteins, and cellular structures. Since fluorophores typically absorb and re-emit Stokes-shifted radiation regardless of being bound or unbound to a species to be detected, the bound and unbound fluorophores must be separated.

One common method to separate the bound fluorophores from the unbound fluorophores relies on spatial localization of the fluorescently labeled species. For example, in a 'sandwich immunoassay' a surface is chemically treated to bind a species to be detected to the surface. The fluorescent probes then attach to the species that are bound to the surface. Unbound fluorophores can then be removed from the system with a wash step.

Background fluorescence can be further reduced if the excitation light can be confined to the surface. Total internal reflection fluorescence (TIRF) is one method of reducing background fluorescence. In general, when light propagates from one medium to another, a portion of the light will be reflected at the interface. If the light is propagating into a material with a lower index of optical refraction, however, all the light will be reflected if the angle at which the beam is incident on the surface is greater than the 'critical angle' (relative to the surface normal). In the lower index material, the light intensity exponentially decays with distance from the surface. This exponentially decaying field—known as an 'evanescent field'—has a characteristic decay length on the order of 100 nanometers to 1 micrometer for visible light. The light of the evanescent field will, therefore, only excite fluorophores that are localized at the surface.

In a simplified implementation, TIRF is performed with a laser beam reflecting once from the surface. This is the basis of well established TIRF microscopy and other biosensing techniques. By confining the laser beam inside a waveguide, however, multiple reflections can be realized and larger areas can be illuminated. Several waveguide geometries are possible, each having certain tradeoffs.

Single-mode planar waveguides, also called thin film waveguides or integrated optical waveguides, confine light into a small cross sectional area with the thin dimension smaller than the wavelength of propagating light. The advantage of single-mode waveguides is that significantly stronger evanescent fields are generated. A disadvantage of single-mode waveguides is that for efficient light coupling, they typically require a prism or grating with precise alignment tolerances. In addition, single-mode planar waveguides are expensive to manufacture because the guiding layer is typically a thin-film with strict thickness tolerances deposited on a substrate. In contrast, a multimode planar waveguide is substantially easier to couple a laser beam to and simpler to construct than single-mode planar waveguides. For example, a standard 1 millimeter thick microscope slide makes an effective waveguide to which light can be coupled through the edge of the slide. Additionally, dimensions for multimode waveguides are compatible with current plastic injection-molding techniques.

For a fluorescence-based assay system, a uniform evanescent field is desired in the detection region. By definition, the strength of the evanescent field is uniform along the direction of light propagation for a single-mode planar waveguide (neglecting scattering losses and absorption inside the waveguide). For a disposable clinical device, however, cost, robustness, and ease of use are of similar importance. By adjusting input coupling to a multimode waveguide, uniformity and field strength can be optimized.

While each individual mode in a multimode waveguide has a uniform intensity along the direction of propagation, a distribution of modes will be excited when coupling to a multimode waveguide; this distribution of modes will constructively and destructively interfere on the surface and lead to a spatially varying field strength. When the thickness of the waveguide is much larger than the wavelength of light, the mode structure of the waveguide can be neglected, and the intensity in the waveguide can be treated as a conventional diffracting beam that totally-internally reflects from the two surfaces of the waveguide and interferes with neighboring reflections.

FIG. 1 illustrates several examples of existing coupling schemes 105-115 involving multimode waveguides. The coupling scheme 105 using a multimode waveguide 120 involves focusing a laser beam 125 that propagates parallel to the waveguide 120 into the edge of the waveguide 120 with a cylindrical lens 130. The field strength of a TIR beam, however, is maximized for a beam that is incident at the critical angle and zero for a beam with an incident angle 90° from the surface normal (i.e., grazing incidence). Thus, an incident beam that is parallel to the TIR surface will have small evanescent field strength when coupled to the waveguide 120 with the cylindrical lens 130 in the configuration of the scheme 105.

A variation on the coupling scheme 105 is illustrated by the coupling scheme 110. In the scheme 110, a laser beam 135 focused by a cylindrical lens 140 is incident on the edge of a waveguide 145 with an appropriate angle such that the central ray of the beam 135 inside the waveguide impinges on the surface near the critical angle for TIR to maximize the evanescent field strength. A compromise between field strength and uniformity may be made by the choice of focusing optics. If a nearly collimated beam is used to achieve high field intensity by operating near the critical angle for TIR, the beam must make many reflections within the waveguide before the surface intensity becomes sufficiently uniform, thus requiring a longer waveguide. If the beam is highly focused, however, then the surface intensity normalizes in very few reflections, but a significant amount of power is contained in rays propagating outside the critical angle and leads to reduced evanescent field strength down the length of the waveguide.

Precise alignment of a cylindrical lens, such as the lenses 130 and 140, relative to the input face of a waveguide, such as the waveguides 120 and 145, respectively, must be made in order to have a laser beam focused on the input face. One proposed solution to this problem is illustrated by the coupling scheme 115. In the coupling scheme 115, a lens 150 is incorporated with a waveguide 155 as a single optical component, made, for example, by bonding the lens element to the planar waveguide or by molding a single optical component. While this allows the focus of the lens 150 to be precisely distanced from the edge of the waveguide 155, careful alignment of a laser beam 160 relative to the lens 150 of the waveguide 155 must still be made to couple the beam 160 to the waveguide 155. For applications requiring repeated placement of a waveguide component relative to the light source, it is highly desirable for the light coupling to be relatively insensitive to misalignment.

SUMMARY OF THE CLAIMED INVENTION

Embodiments of the present invention allow light to be coupled to a planar waveguide providing a strong evanescent field for sample illumination, while eliminating or greatly reducing inadvertent misalignment by a user. Embodiments of the present invention further allow facile tuning of the internal propagation angle inside the waveguide, providing simple adjustment of evanescent field strength. Embodiments of the present invention also provide apparatus for performing assays involving placement of a fluidic chamber on a planar waveguide in a manner that is insensitive to the optical properties of the chamber.

In a claimed embodiment, apparatus for illuminating a sample for analysis is disclosed. The apparatus includes a light source, a planar waveguide, and a refractive volume. The light source provides light along a propagation vector. The planar waveguide is oriented such that the propagation vector is perpendicular to the normal vector of the planar waveguide and offset from the planar waveguide in a direction parallel to the normal vector of the planar waveguide. The refractive volume, which is positioned proximate to the planar waveguide, optically couples light provided by the light source to the planar waveguide.

Another claimed embodiment sets forth a method for performing sample analysis. Light is provided from a light source along a propagation vector. A refractive volume positioned proximate to a planar waveguide is illuminated with the light. The waveguide is oriented such that the propagation vector is perpendicular to the normal vector of the planar waveguide and offset from the planar waveguide in a direction parallel to the normal vector of the planar waveguide. The light is then coupled to the planar waveguide via the refractive volume.

Apparatus for performing biological assays is disclosed in yet another claimed embodiment. The apparatus includes a light source, a planar waveguide, a refractive volume, and a detector. The light source provides light along a propagation vector. The planar waveguide has a plurality of specific binding molecules bound to a face thereof. The planar waveguide could further have an array of two or more dissimilar specific binding molecules bound to the face thereof. Additionally, the optical axis of the planar waveguide is oriented parallel to the propagation vector and offset from the propagation vector in a direction perpendicular to a face of the planar waveguide. The refractive volume optically couples light provided by the light source to the planar waveguide and is positioned proximate to the planar waveguide. The refractive volume includes at least a section of a plano-convex cylindrical lens. The detector is positioned to detect light emitted from a region proximate to the face of the planar waveguide having the plurality of specific binding molecules bound thereto.

DETAILED DESCRIPTION

Embodiments of the present technology provide for sample illumination such as that involved in fluorescence detection and assay based on evanescent fields using apparatus comprising a waveguide with an integrated lens. The overall configuration of the apparatus may be such that fluorescence-emitting molecules bound to a waveguide surface are excited by an evanescent field penetrating into the adjacent solution from a light beam propagated within the waveguide, the propagated beam being introduced by an integrally connected lens. The collimated beam of light such as a laser beam may propagate parallel to the waveguide surface such that the system is insensitive to translation of the waveguide. The incident beam may be also appropriately offset from the optical axis of the waveguide such that refraction of the light at the lens surface directs the beam into the waveguide at an angle close to the critical angle for TIR. Additionally, a second integrated cylindrical lens may be added to the output end of the waveguide. This may facilitate a second laser being coupled in the opposite direction, such as for multi-color fluorescence assays.

The apparatus may also allow a fluidic chamber to be bound to the planar waveguide such that the chamber contact with the planar waveguide is outside the optical path of the propagating light, eliminating restrictions on optical properties of material comprising the chamber. In some previous configurations, fluidic chambers have utilized low index of refraction materials in contact with the planar waveguide with mechanical clamping in order to limit optical losses at the waveguide/chamber contact area. By separating the waveguide/chamber contact from the optical path, traditional bonding methods such as adhesives or plastic welding can be used to attach the chamber to the waveguide. Moreover, the fluidic chamber may comprise or be formed in part by a second planar waveguide, wherein the fluidic chamber is disposed between two planar waveguides. In such an arrangement light may be coupled to both planar waveguides as well as the volume formed by the fluidic chamber.

Figure 1:
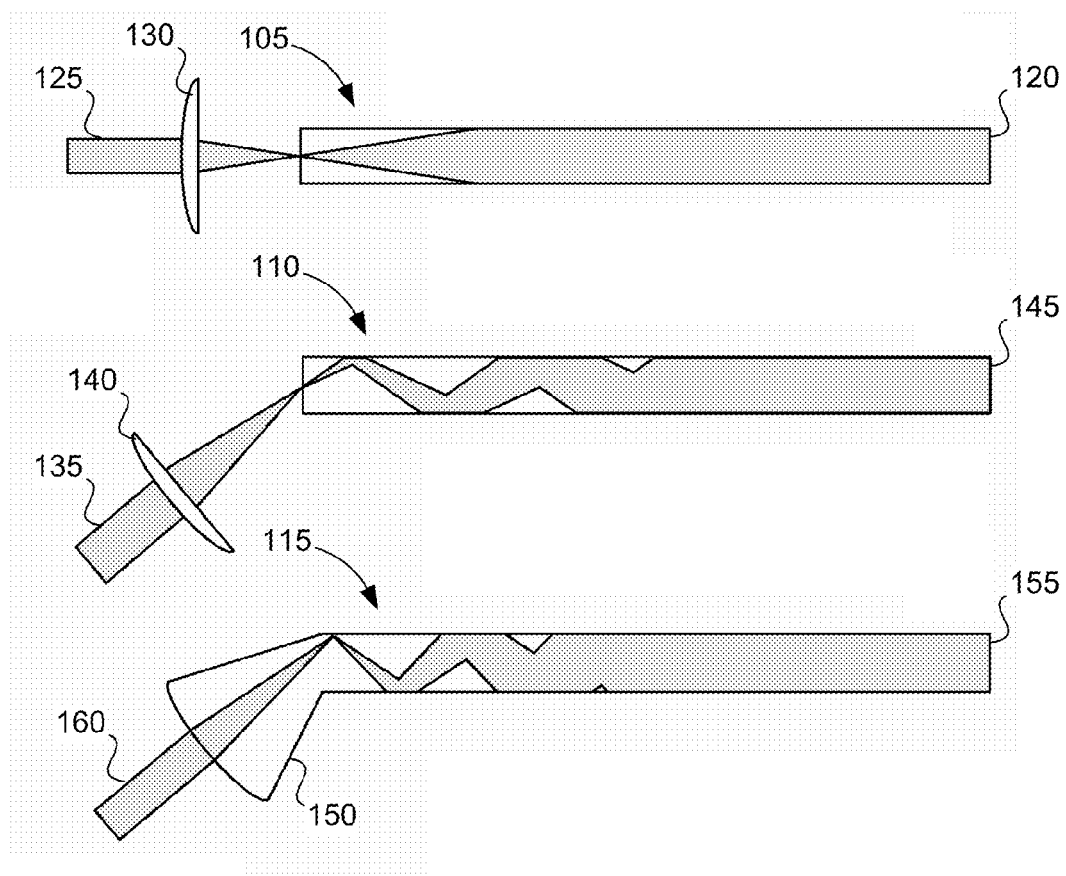
FIG. 1 illustrates several examples of existing coupling schemes involving multimode waveguides.
Figure 2:
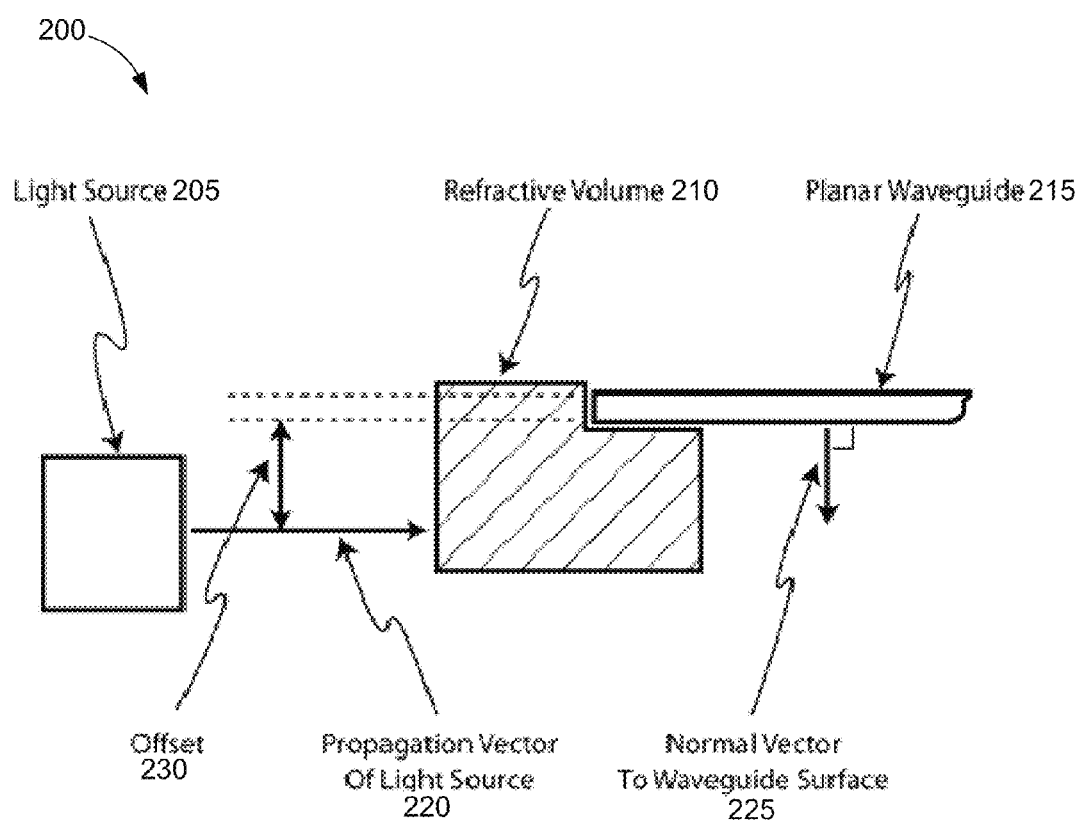
FIG. 2 illustrates a generalized configuration descriptive of exemplary embodiments.

FIG. 2A illustrates a generalized configuration 200 descriptive of exemplary embodiments. The configuration 200 includes a light source 205, a refractive volume 210, and a planar waveguide 215. The light source 205 can include a laser or any other source of collimated or near-collimated light that provides light along a propagation vector 220. The refractive volume 210 is positioned proximate to the planar waveguide 215. The refractive volume 210 and the planar waveguide 215 may lack a discontinuity in index of refraction therebetween. For example, the refractive volume 210 may be adjacent to or abutted to the waveguide 215 with an index matching fluid occupying any gap therebetween. Alternatively, the refractive volume 110 may be integrated with the planar waveguide 215 as a single unit or article. The planar waveguide 215 is oriented such that the propagation vector 220 is perpendicular to the normal vector 225 of the planar waveguide 215. Furthermore, the planar waveguide has an offset 230 in a direction parallel to the normal vector 225 of the planar waveguide 215.

Figure 3:
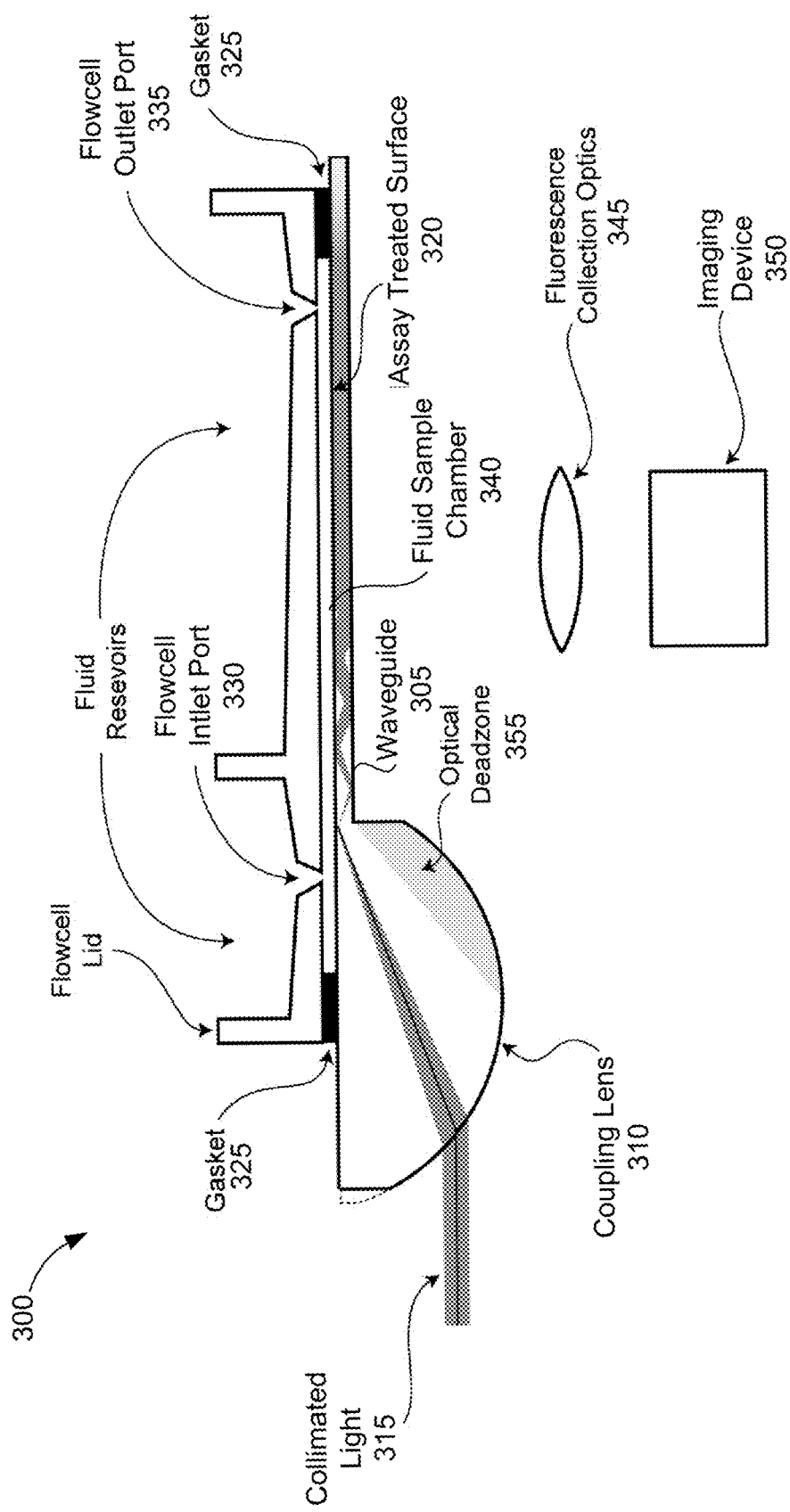
FIG. 3 illustrates a cross-sectional view of an exemplary waveguide with an integrated lens.

FIG. 3 illustrates an exemplary cross-sectional view 300 of a waveguide 305 with an integrated lens 310 according to one embodiment. Additionally, the view 300 depicts a collimated light beam 315 such as that of a laser with a wavelength appropriate to excite fluorescent probes at an assay surface 320. The planar waveguide 305 with the associated lens 310 is configured to inject the excitation light 315 through the bottom of the planar waveguide 305. A flowcell comprising a sealing mechanism such as a gasket 325, an inlet port 330, an output port 335, and a fluid sample chamber 340 in which chemical compounds deposited on the top surface 320 of the waveguide may bind the desired target compound to the surface. Collection and filtering optics 345 can capture fluorescence from the top surface 320 of the waveguide. The fluorescence signal can then be directed to an imaging device 350 such as a CCD or CMOS camera. Furthermore, the roof, the floor, and/or the walls of the flow cell may be used as a surface on which compounds are deposited.

It is noteworthy that the fluidic sample chamber 340 may comprise or be formed in part by a second planar waveguide, similar to the waveguide 305, such that the fluidic sample chamber 340 is disposed between two planar waveguides. In such a configuration, light may be coupled to both planar waveguides as well as the volume formed by the fluidic sample chamber 340. The principles described herein are similarly applicable to configurations having multiple planar waveguides.

Figure 4:
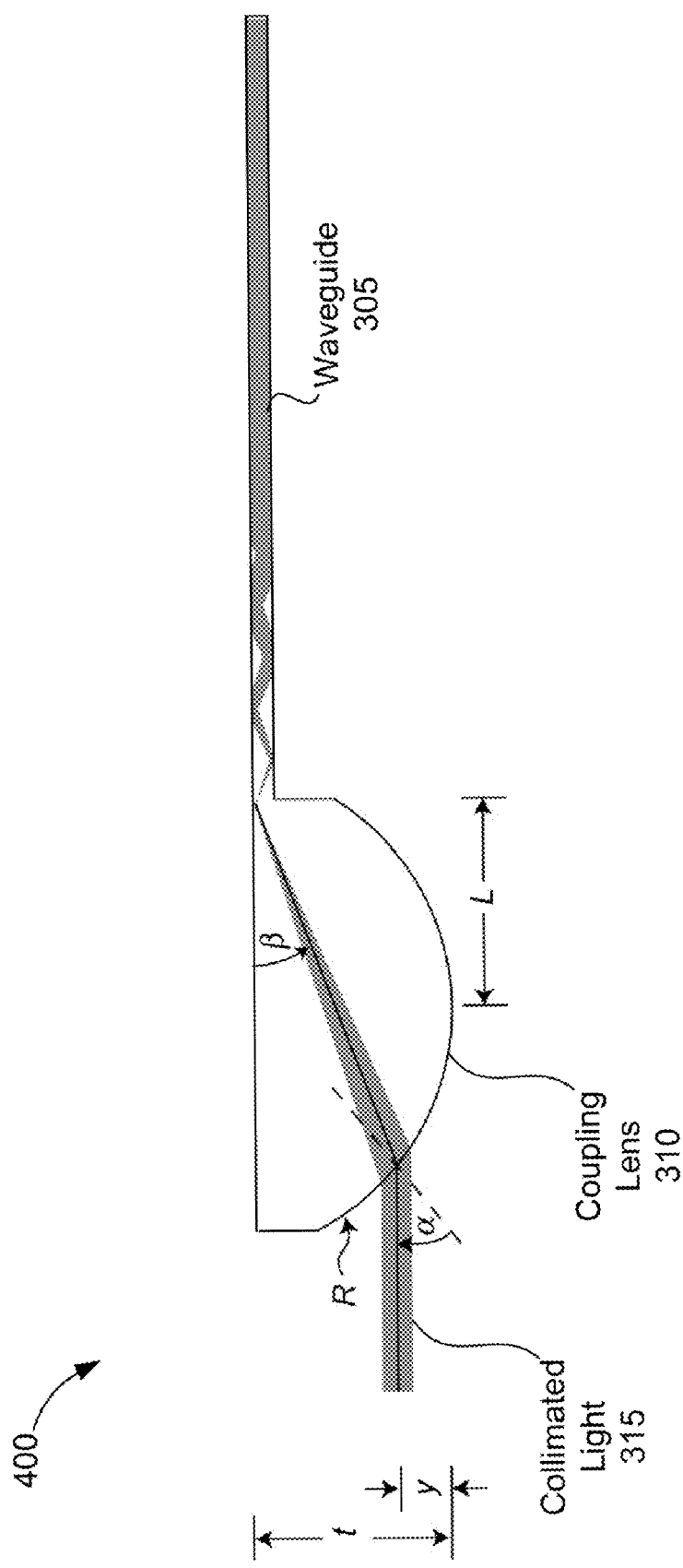
FIG. 4 provides a detailed cross-sectional view of the waveguide with the integrated lens depicted in FIG. 3.
Figure 5:
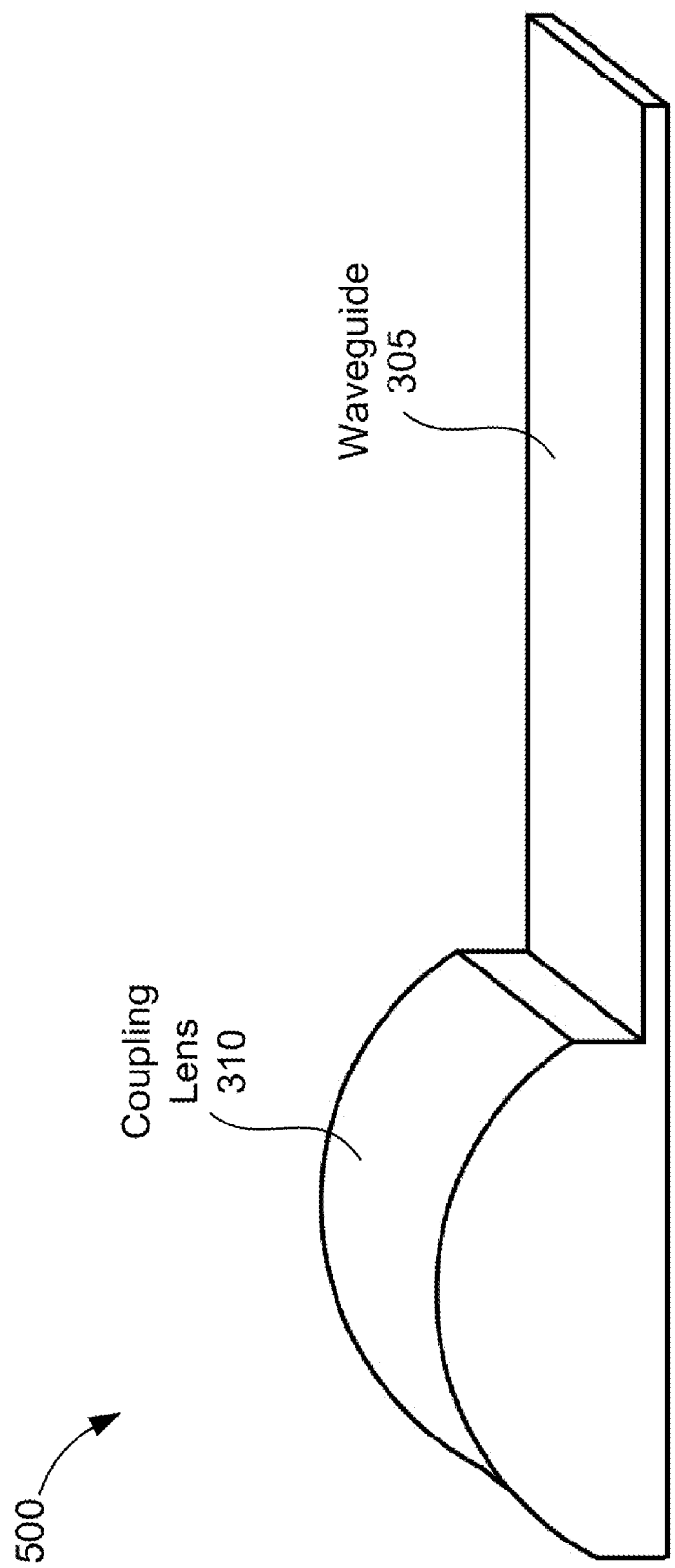
FIG. 5 is a cavalier projection view illustrating the exemplary waveguide with the integrated lens.

FIG. 4 provides a detailed cross-sectional view 400 of the waveguide 305 with the integrated lens 310. For further reference, FIG. 5 is a cavalier projection view 500 illustrating the exemplary waveguide 305 with the integrated lens 310. Referring back to FIG. 4, the collimated light beam 315 propagates in a direction parallel or nearly parallel to the optical axis of the planar waveguide 305, but offset from the optical axis such that it strikes the curved surface of the cylindrical lens 310. For a clinical instrument in which the waveguide structure is a removable consumable item, this geometry may loosen the positional tolerances necessary to couple the collimated light 315 reproducibly to the waveguide 305. The light 315 impinges on the curved surface of the lens 310 at a non-zero angle α relative to the local surface normal of the lens 310, as illustrated in FIG. 4.

As a result of refraction explained by Snell's law, the light beam 315 refracts such that it strikes the top surface of the waveguide 305 at an angle β relative to the optical axis of the waveguide 305. The angle β is defined as the internal propagation angle. The vertical distance y between the center of the light beam 315 and the apex of the cylindrical lens 310 is chosen such that β is less than the complement of the critical angle allowing total internal reflection to occur. For a given radius R for the curved surface of the lens 310 and index of refraction n for the cylindrical lens 310, the distance y and angle β are related by the equation:

$$y = R\left[1 - \frac{n\sin\beta}{\sqrt{1 - 2n\cos\beta + n^2}}\right].$$

Since the light beam 315 has a spatial extent, the curved surface of the lens 310 will act to focus the light beam 315. The radius R of the curved surface of the lens 310 is chosen such that for a given beam diameter of the light beam 315, the range of angles incident on the top surface of the waveguide 305 is appropriate to provide a uniform evanescent field strength within the detection region while remaining outside the critical angle for TIR. It may be desired that the light beam 315 focus on the top surface of the waveguide 305 to allow for the greatest tolerance to misalignment. The total thickness t for the structure comprising the waveguide 305 and lens 310 that leads to a focused beam on the top surface may be given by:

$$t = R + \frac{(y - R)^3}{R^2 n^2}.$$

When an appropriate thickness t is used, the light beam 315 will focus at a horizontal distance L from the center of the circle defining the curved surface of the lens 310. L may be related to the previously defined quantities by the equation:

$$L = \frac{t - y}{\tan\beta} - \sqrt{2yR - y^2}.$$

The structure comprising the waveguide 305 and lens 310 may be manufactured in several different ways. One method is to have the entire assembly constructed in plastic by injection molding technology. An alternative method is to fabricate the planar waveguide and lens element separately from similar index materials. The two elements may then be joined permanently by a transparent optical cement, optical contacting, or temporarily with index matching fluid/oil/gel.

Geometries such as those described in connection with FIG. 3 easily allow the adjustment of the internal propagation angle (β) through a translation, rather than a rotation, of the incident laser beam. This allows for a less complicated mechanical design to couple the laser to the waveguide. Additionally, a new injection molded waveguide is not necessary when it is desired to change the incident angle because the focal point of the lens using the disclosed geometry of FIGS. 3 and 4 is very insensitive to the translation of a laser beam relative to the optical axis of the waveguide 305. Further, a desired change in the incident angle is accomplished without changing the readout instrument, allowing variation of cartridge function without physical changes in the instrument. A barcode on the cartridge may be utilized to identify information used to interpret signals from a given cartridge.

To prevent light from leaking from the waveguide 305 after the first reflection from the top surface, the cylindrical lens 310 is truncated such that it does not extend beyond the location of the focus. The area defined by the line connecting the apex of the cylindrical lens 310 and the point on the bottom surface opposite the focus (see, e.g., 'optical deadzone 355' in FIG. 3) will never have light propagate in it that successfully couples to the waveguide. As such, the precise shape of the lens in the area designated optical deadzone 355 can comprise any convenient shape provided the lens 310 does not extend beyond the vertical line passing through the focus. For a single injection molded device where minimizing material costs is important, removing all plastic in the area labeled optical deadzone 355 may be desirable. If two separate components made through conventional optical manufacturing processes are fabricated, a traditional cylindrical lens 310 that has been diced to remove material beyond the focus can be easily manufactured. A material that has low autofluorescence properties may be desirable to minimize background contributions in the signal collection.

Because the cylindrical lens 310 is used in off-axis geometry, minor optical aberrations at the focus may be exhibited if the curved surface is circular. While a circular profile functionally works, the use of an aspheric surface may be employed to extend the range of the vertical position of the incident beam for which the beam will be coupled to the planar waveguide 305, allowing a larger range of adjustment of the angle β. The appropriate deviation from a circular profile can be calculated with optical ray tracing programs familiar to those skilled in the art.

The large area of the top surface of the waveguide 305 before the focus may allow for a sample chamber to be sealed. The gasket 325 sealing surface may be absent from the optical path. Therefore, a larger range of gasket materials may be possible that only need to be evaluated for their chemical/biological compatibility and not their optical properties. For example, an adhesive backed spacer can be utilized to form a sealed flowcell without a complicated clamping mechanism. Multiple flow cells can also be incorporated into a single biosensor by utilizing a gasket with multiple channels.

Figure 6:
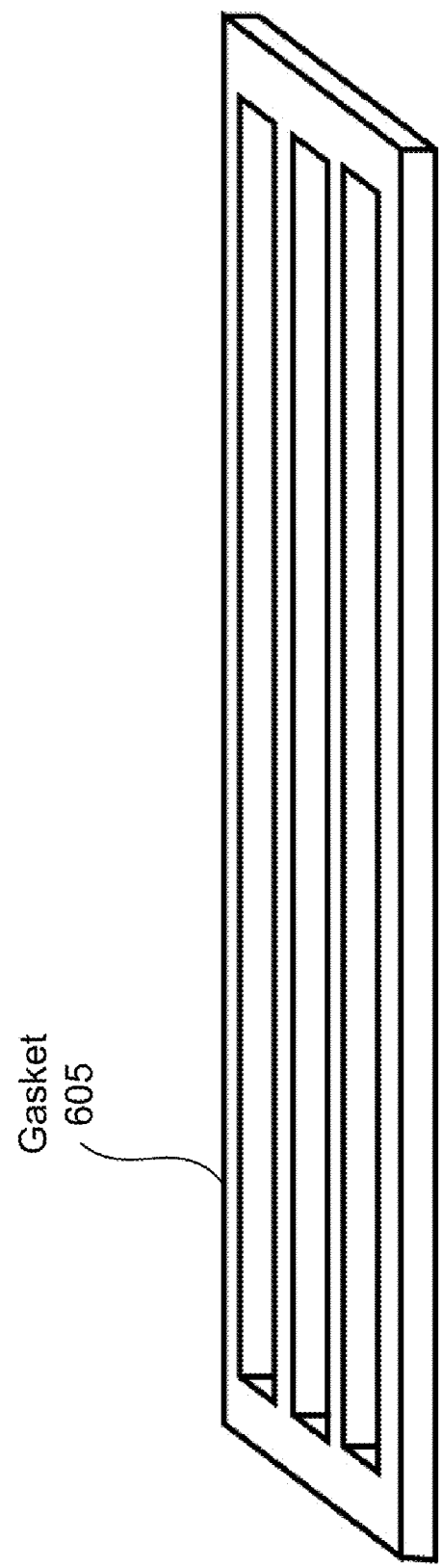
FIG. 6 is a cavalier projection view illustrating an exemplary gasket with multiple channels.

FIG. 6 is a cavalier projection view illustrating an exemplary gasket 605 with multiple channels. The width of the channel may be chosen to match the unfocused dimension of the incident beam such that light coupling to the gasket along the length of the waveguide is minimized. A mechanism for translating the incident beam between channels may be included. In addition, the top surface of the waveguide 305 within the flow channels may be appropriately treated to allow for the capture of fluorescently labeled target molecules such as proteins, RNA, DNA, or cellular structures.

A lid attached to the gasket completes the flow cell. Fluid samples can be introduced through orifices in the lid and flow through the channels, allowing the fluid to interact with the top waveguide surface. Fluid reservoirs exterior to the flow channel can also be included to allow the introduction of fluids into the flow channel and an overflow reservoir at the outlet port of the flow channel to contain the fluid after it has passed through the flow channel. With plastic components, the gasket can be optionally eliminated by molding the channels into one of the plastic components and joining the two plastic components directly with methods known to those skilled in the art (e.g., laser or ultrasonic welding).

The evanescent field created by the light within the waveguide 305 can excite fluorophores that have attached to the top surface of the waveguide 305. As the fluorophores relax and emit frequency shifted radiation, the emitted light may be captured by a lens or series of lenses (e.g., the collection optics 345) to transfer an image of the surface to a plane that is imaged by a light capturing device (e.g., the imaging device 350) such as a CCD or CMOS sensor. An optical filter can also be placed between the waveguide surface and the imaging device to eliminate scattered incident light that has not been frequency shifted by the captured fluorophores.

Figure 7:
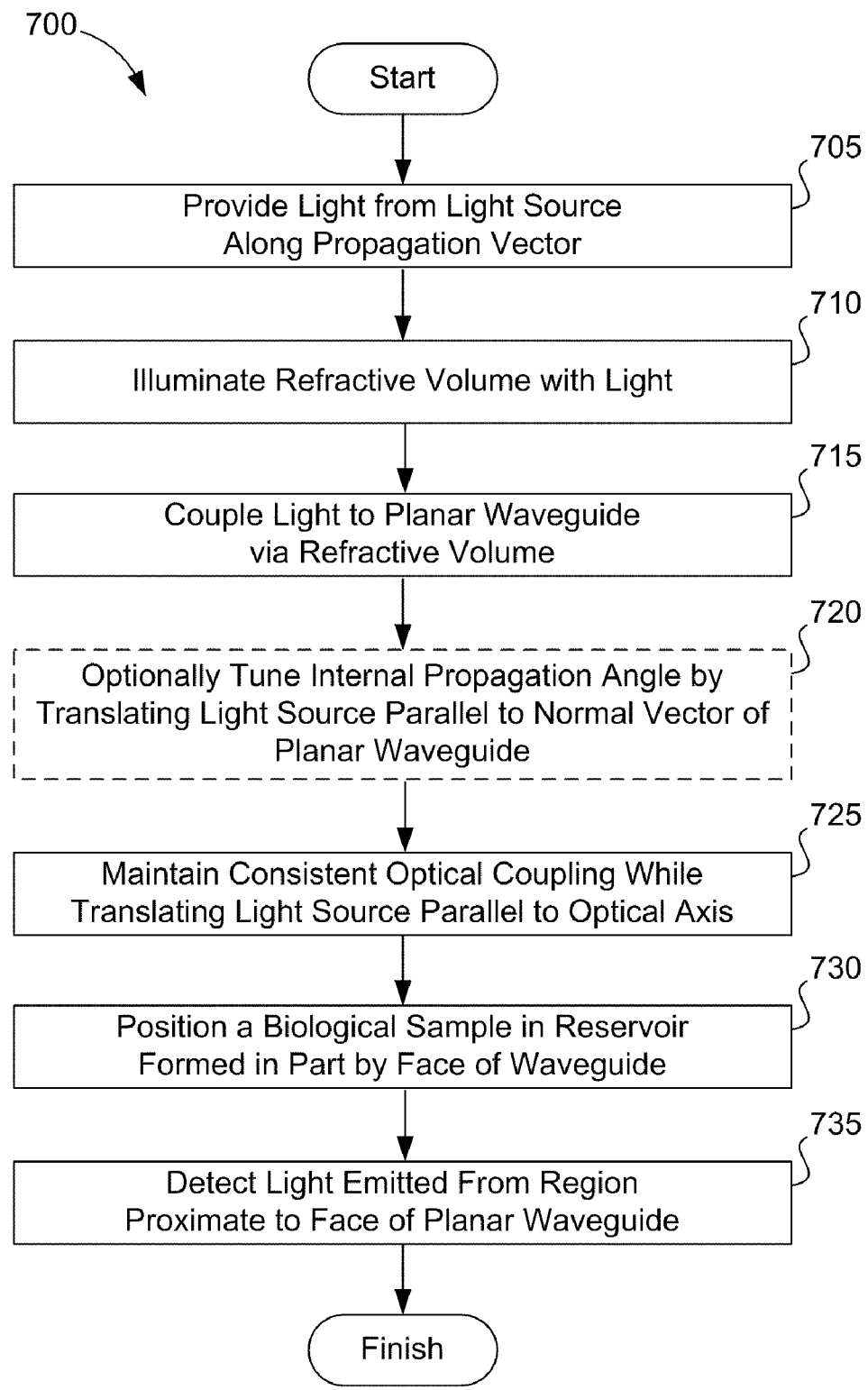
FIG. 7 is a flowchart of an exemplary method for performing sample analysis.

FIG. 7 is a flowchart of an exemplary method 700 for performing sample analysis. The steps of the method 700 may be performed in varying orders. Furthermore, steps may be added or subtracted from the method 700 and still fall within the scope of the present technology. The methodology illustrated in FIG. 7 may be performed for fluorescence detection and assay based on evanescent fields.

In step 705, light is provided from a light source along a propagation vector. The light source can include a laser or any other source of collimated or near-collimated light.

In step 710, a refractive volume is illuminated with the light. The refractive volume is positioned proximate to, and may be integrated with, a planar waveguide. In exemplary embodiments, the refractive volume may include at least a section of a plano-convex cylindrical lens, wherein the longitudinal axis of the refractive volume is oriented perpendicular to the optical axis and the normal vector of the planar waveguide.

In step 715, the light is coupled to the planar waveguide via the refractive volume. The waveguide is oriented such that the propagation vector is perpendicular to the normal vector of the planar waveguide and offset from the planar waveguide in a direction parallel to the normal vector of the planar waveguide.

In optional step 720, the optical coupling of the light provided by the light source to the planar waveguide is tuned by translating the light source in a direction parallel to the normal vector of the planar waveguide.

In step 725, consistent optical coupling of the light provided by the light source to the planar waveguide is maintained while translating the light source parallel to the optical axis of the planar waveguide.

In step 730, a biological sample is positioned in a reservoir formed at least in part by a face of the planar waveguide.

In step 735, light emitted from a region proximate to a face of the planar waveguide is detected. In some embodiments, a detector is positioned to detect light emitted from a region proximate to the face of the planar waveguide having a plurality of capture molecules bound thereto.

The present invention has been described above with reference to exemplary embodiments. It will be apparent to those skilled in the art that various modifications may be made and other embodiments can be used without departing from the broader scope of the invention. Therefore, these and other variations upon the exemplary embodiments are intended to be covered by the present invention.

What is claimed is:

1. Apparatus for illuminating a sample for analysis, the apparatus comprising:
    a light source for providing a light beam along a propagation vector, the light beam having a beam diameter;
    a planar waveguide oriented such that the propagation vector is perpendicular to the normal vector of the planar waveguide and the light beam is offset from the planar waveguide in a direction parallel to the normal vector of the planar waveguide; and
    a refractive volume for optically coupling the light beam to the planar waveguide, the refractive volume positioned proximate to the planar waveguide;
    wherein the refractive volume is configured for refracting the light beam such that the light beam strikes a planar surface of the planar waveguide at a non-zero internal propagation angle relative to an optical axis of the planar waveguide for all light within the beam diameter, and
    wherein an internal propagation angle of the light beam in the planar waveguide is tuned by a relative translation of the light source in a direction parallel to the normal vector of the planar waveguide.

2. The apparatus of claim 1, wherein a relative translation of the light source parallel to the optical axis of the planar waveguide is inconsequential to the optical coupling of the light beam to the planar waveguide.

3. The apparatus of claim 1, wherein the planar waveguide has a plurality of capture molecules bound to a face thereof.

4. The apparatus of claim 1, further comprising a detector positioned to detect light emitted from a region proximate to a face of the planar waveguide.

5. The apparatus of claim 1, wherein the refractive volume comprises at least a section of a plano-convex cylindrical lens.

6. The apparatus of claim 1, wherein the light source includes one or more of a laser, a white light source, or a light emitting diode.

7. The apparatus of claim 1, wherein the refractive volume is shaped to minimize an optical aberration.

8. The apparatus of claim 1, wherein the planar waveguide and the refractive volume are integrated as a single article.

9. The apparatus of claim 1, wherein the refractive volume and the planar waveguide lack a discontinuity in index of refraction therebetween.

10. The apparatus of claim 1, further comprising a fluidic chamber, a first side of the fluidic chamber abutted to a face of the planar waveguide having a plurality of capture molecules bound thereto.

11. The apparatus of claim 10, wherein a region defined at least partially by the face of the planar waveguide having the plurality of specific binding molecules bound thereto and the fluidic chamber forms a reservoir for biological samples.

12. A method for performing sample analysis, the method comprising:
    providing a light beam from a light source along a propagation vector, the light beam having a beam diameter;
    illuminating a refractive volume positioned proximate to a planar waveguide with the light beam;
    coupling the light beam to the planar waveguide via the refractive volume; and
    tuning the optical coupling of the light beam to the planar waveguide by translating the light source in a direction parallel to the normal vector of the planar waveguide,
    wherein the planar waveguide is oriented such that the propagation vector is perpendicular to the normal vector of the planar waveguide and the light beam is offset from the planar waveguide in a direction parallel to the normal vector of the planar waveguide, and
    wherein the refractive volume is configured for refracting the light beam such that the light beam strikes a planar surface of the planar waveguide at a non-zero internal propagation angle relative to an optical axis of the planar waveguide for all light within the beam diameter.

13. The method of claim 12, further comprising maintaining consistent optical coupling of the light beam to the planar waveguide while translating the light source parallel to the optical axis of the planar waveguide.

14. The method of claim 12, further comprising positioning a biological sample in a reservoir formed at least in part by a face of the planar waveguide.

15. The method of claim 12, further comprising detecting light emitted from a region proximate to a face of the planar waveguide.

16. Apparatus for performing biochemical assays, the apparatus comprising:
    a light source for providing a light beam along a propagation vector, the light beam having a beam diameter;
    a planar waveguide having a plurality of capture molecules bound to a face thereof, the optical axis of the planar waveguide oriented parallel to the propagation vector and offset from the light beam in a direction perpendicular to a face of the planar waveguide;
    a refractive volume for optically coupling the light beam to the planar waveguide, the refractive volume positioned proximate to the planar waveguide and comprising at least a section of a plano-convex cylindrical lens, the longitudinal axis of the refractive volume being oriented perpendicular to the optical axis of the planar waveguide; and
    a detector positioned to detect light emitted from a region proximate to the face of the planar waveguide having the plurality of capture molecules bound thereto;
    wherein the refractive volume is configured for refracting the light beam such that the light beam strikes a planar surface of the planar waveguide at a non-zero internal propagation angle relative to the optical axis of the planar waveguide for all light within the beam diameter.

17. Apparatus for illuminating a sample for analysis, the apparatus comprising:
    a light source for providing a light beam along a propagation vector, the light beam having a beam diameter; and
    a waveguide, including a refractive volume upon which the light beam impinges, and forming a planar surface that is parallel with the propagation vector,
    wherein the refractive volume couples the light beam into the waveguide such that the light beam focuses on the planar surface at a non-zero internal propagation angle relative to the planar surface, for all light within the beam diameter.

18. The apparatus of claim 17,
    wherein the waveguide further comprises a detection region over a portion of the planar surface, and
    wherein the internal propagation angle is such that the light beam results in illumination of the planar surface with a uniform evanescent field strength within the detection region.

19. The apparatus of claim 17, wherein a relative translation of the light source parallel to the planar surface does not affect focusing of the light beam on the planar surface at the non-zero, internal propagation angle.

20. The apparatus of claim 17, wherein the waveguide is integrally formed of a single optical material.

21. The apparatus of claim 17, wherein the waveguide is formed by coupling the refractive volume with a planar waveguide that forms the planar surface.

22. The apparatus of claim 17, further comprising a fluidic chamber, the fluidic chamber being partially defined by the planar surface.

23. The apparatus of claim 22, wherein the planar surface includes a plurality of capture molecules bound thereto such that, when a fluid is introduced into the fluidic chamber, the fluid comes into contact with the plurality of capture molecules.

24. The apparatus of claim 17, the refractive volume comprising a section of a plano-convex cylindrical lens, a planar surface of the plan-convex cylindrical lens being parallel with the planar surface.

25. The apparatus of claim 24, wherein:
    the light source is arranged with respect to the planar waveguide such that all light within the beam diameter is offset from the planar surface in a direction perpendicular to the planar surface, and
    the light beam impinges upon a convex surface of the plano-convex cylindrical lens so as to refract towards the planar surface.

26. A method for illuminating a sample at a planar surface of a planar waveguide, the method comprising:
provides a light beam along a propagation vector parallel to the planar surface, the light beam having a beam diameter;
refracting the light beam so as to direct all light within the beam diameter upon the planar surface at a non-zero internal propagation angle relative to the planar surface; and
tuning the internal propagation angle by translating the light beam in a direction parallel to a normal vector of the planar waveguide.

27. The method of claim 26, the planar surface including a detection region,
wherein refracting further comprises directing the light beam such that the internal propagation angle is less than a complement of a critical angle for total internal reflection at the planar surface.

28. The method of claim 27, wherein refracting comprises illuminating a refractive volume that is integrally formed with the planar waveguide, with the light beam.

29. The method of claim 26, wherein refracting comprises illuminating a convex surface of a plano-convex cylindrical lens portion that forms the refracting volume, a planar surface of the plano-convex cylindrical lens being parallel with the propagation vector and coplanar with the planar surface.

30. The method of claim 26, wherein translation of the light beam in a direction parallel to an optical axis of the planar waveguide does not affect the internal propagation angle.

31. The method of claim 26, the planar surface including a detection region, the method further comprising detecting signal from the detection region in a plane parallel to the planar surface.

32. The apparatus of claim 1, the internal propagation angle providing a uniform evanescent field strength at a detection region of the planar waveguide.

33. The apparatus of claim 12, wherein coupling comprises refracting the light beam such that the internal propagation angle provides a uniform evanescent field strength at a detection region of the planar waveguide.

34. The apparatus of claim 16, the internal propagation angle providing a uniform evanescent field strength at a detection region of the planar waveguide.

35. A waveguide for use in performing biochemical assays, comprising:
a planar waveguide having an upper planar surface with a detection region forming a portion thereof, and a lower planar surface counterfacing the upper planar surface; and
a refractive volume comprising a section of a plano-convex cylindrical lens, a planar surface of the lens being coplanar with one of the upper and lower planar surfaces of the planar waveguide;
wherein when a collimated light beam is arranged with respect to the waveguide such that (a) the light beam propagates parallel to the planar surface of the planar waveguide, (b) the light beam impinges upon the refractive volume, and (c) the light beam is offset from the planar surface such that without the refractive volume, no part of the light beam would impinge upon the planar waveguide;
the refractive volume refracts the light beam towards the planar waveguide such that all of the light within the light beam impinges upon the upper planar surface at a non-zero angle, and propagates within the planar waveguide by total internal reflection.

36. A waveguide for use in performing biochemical assays, comprising:
a planar waveguide having an upper planar surface with a detection region forming a portion thereof, and a lower planar surface counterfacing the upper planar surface; and
a refractive volume comprising a section of a plano-convex cylindrical lens, a planar surface of the lens being coplanar with one of the upper and lower planar surfaces of the planar waveguide;
wherein when a collimated light beam is arranged with respect to the waveguide such that (a) the light beam propagates parallel to the planar surface of the planar waveguide, (b) the light beam impinges upon the refractive volume, and (c) the light beam is offset from the planar surface such that without the refractive volume, no part of the light beam would impinge upon the planar waveguide;
the refractive volume refracts the light beam towards the planar waveguide such that all of the light within the light beam impinges upon the upper planar surface at a non-zero angle, and propagates within the planar waveguide by total internal reflection; and
wherein a total thickness t of the waveguide, measured perpendicularly from the upper planar surface, is given by $$t = R + \frac{(y-R)^3}{R^2 n^2};$$

where
R is a radius of the lens,
y is an offset of the light beam, measured perpendicularly with respect to the upper planar surface from an apex of the lens, and
n is an index of refraction of the lens;
such that the lens focuses the beam on the planar surface.

37. The apparatus of claim 17, wherein the refractive volume causes the light beam to diverge as it progresses through the waveguide after focusing on the planar surface.

38. The apparatus of claim 35, wherein the refractive volume causes the light beam to diverge as it progresses through the waveguide after impinging on the upper planar surface.

* * * * *